United States Patent [19]

Shinnick et al.

[11] Patent Number: 4,689,397
[45] Date of Patent: Aug. 25, 1987

[54] SYNTHETIC POLYPEPTIDES FOR DETECTING MYCOBACTERIAL INFECTIONS

[75] Inventors: Thomas M. Shinnick, Del Mar; Percy Minden, La Jolla; Richard A. Houghten, Solana Beach, all of Calif.

[73] Assignee: Scripps Clinic and Research Foundation, La Jolla, Calif.

[21] Appl. No.: 765,048

[22] Filed: Aug. 12, 1985

[51] Int. Cl.$^4$ .......................... C07C 7/08; C07C 7/10
[52] U.S. Cl. .................................. 530/327; 530/326; 530/325; 530/324
[58] Field of Search ............... 530/300, 324, 325, 326, 530/337

[56] References Cited

U.S. PATENT DOCUMENTS 3,875,002  4/1975  Landi et al. ........................ 530/300

OTHER PUBLICATIONS

Can. Journal of Microbiology, vol. 24, No. 9 (1978), 1242–1249.
Infection and Immunity, vol. 50 (1985), No. 3, 614–619.
Infection and Immunity, vol. 27, No. 2 (1980), 344–350.
Infection and Immunity, vol. 30 (1980), No. 3, 686–693.
Minden et al., *Infect. Immun.*, 53:560–564 (1985).

Primary Examiner—Delbert R. Phillips
Attorney, Agent, or Firm—Dressler, Goldsmith, Shore, Sutker & Milnamow, Ltd.

[57] ABSTRACT

Antigens, immunogens, inocula, antibodies, diagnostic methods and systems relating to tuberculous mycobacteria are disclosed. Each of the compounds, compositions, methods or systems contains a synthetic polypeptide having about 13 or 14 to about 40 residues, or an antibody containing site that immunoreacts with such a polypeptide. The polypeptide includes the thirteen or fourteen amino acid reside sequence (AlaLysValAsnIleLysProLeuGluAspLysIleCys) or (CysAlaLysValAsnIleLysProLeuGluAspLysIleCys). When linked to a carrier and introduced in an effective amount into a mammalian host, the polypeptide is capable of inducing production of antibodies that immunoreact with an antigen to a tuberculous mycobacterium.

10 Claims, 1 Drawing Figure

Ala-Lys-Val-Asn-Ile-Lys-Pro-Leu-Glu-Asp-Lys-Ile-Leu-Val-Glu-Ala-Asn-Glu-Ala-Glu
1 5 10 15 20

-Ala-Lys-Val-Asn-Ile-Lys-Pro-Leu-Glu-Asp-Lys-Ile-Cys-
1 5 10 12

-Cys-Ala-Lys-Val-Asn-Ile-Lys-Pro-Leu-Glu-Asp-Lys-Ile-Cys-
1 5 10 12

FIGURE 1

SYNTHETIC POLYPEPTIDES FOR DETECTING MYCOBACTERIAL INFECTIONS

The United States Government has rights in this invention pursuant to a grant awarded by the National Institutes of Health.

TECHNICAL FIELD

The present invention relates to immunogens, antigens, inocula, antibodies, methods and systems useful in the detection, diagnosis and treatment of diseases involving mycobacterial infections.

BACKGROUND OF THE INVENTION

Mycobacteria have long been recognized as bacterial pathogens of man and continue to produce devastating illness, particularly in developing countries. World Health Organization, *Bull. WHO*, 61, 779 (1983). Tuberculosis is caused by respiratory infection with *Mycobacterium tuberculosis* (*M. tuberculosis*) and currently afflicts about 30 million people worldwide with an annual mortality of about 3 million.

Crude bacterial antigen preparations have been used for immunodiagnostic and immunoprophylactic purposes. The tuberculin test developed by Koch in 1881 was the first immunodiagnostic test used in man. Tuberculin, an *M. tuberculosis* filtrate of complex but poorly defined composition, is currently used as a delayed-type cutaneous hypersensitivity (DCH) or skin test antigen to detect prior exposure to the pathogen. Seibert et al., *Am. Rev. Tuberc.*, 69, 585 (1954). Unfortunately, the utility of tuberculin is limited both by its lack of specificity and by its inability to distinguish between active disease, prior sensitization by contact with *M. tuberculosis* or cross-sensitization to other mycobacteria.

Bacillus Calmette-Guerin (BCG), an avirulent strain of *Mycobacterium bovis* (*M. bovis*), is currently used as a live vaccine to protect against tuberculosis in man. Calmette, A., *J. Am. Med. Assoc.*, 96, 58 (1931). While BCG has been effective in reducing the incidence of tuberculosis in Western Europe [Medical Research Council, *Bull. WHO*, 46, 371 (1972)], it has recently been found to be ineffective in a major trial in India [World Health Organization, *WHO Tech. Rep. Ser.*, 651 (1980)].

A basic problem with the crude antigen preparations that are now used to detect mycobacterial infections is that the antigen preparations often react positively with several different mycobacterial species. This, of course, complicates diagnosis and the selection of an appropriate treatment regimen. A reagent that specifically evokes an immune response against a particular mycobacterial species would be beneficial in the diagnosis and management of mycobacterial infections.

The advantages of the use of a defined polypeptide antigen in a DCH reaction are numerous. For example, in the case of mycobacterial infections, since the amino acid residue sequence of the polypeptide corresponds to a portion of a protein that is specifically expressed in the tuberculous mycobacterial species, the polypeptide may be a useful reagent for specifically detecting a tuberculous mycobacterial infection and thereby circumventing the cross-reactivity problems associated with the currently-used skin test antigens. Moreover, the polypeptide may be chemically synthesized to eliminate the need to grow large cultures of a pathogenic organism for the production of skin test antigens.

The polypeptide may also be used in the detection or prevention (vaccination) of mycobacterial infections. In fact, an inoculum containing the polypeptide could replace tuberculin or PPD (purified protein derivative) as the antigen of choice in DCH or skin tests for the detection of tuberculosis in humans.

While the general concept of preparing synthetic antigens (immunogens) and using them to induce antibodies of predetermined specificity has been described, there remains a large area of this technology that continues to defy predictability. There are at least two reasons for this. First, a synthetic antigen (immunogen) does not necessarily induce antibodies that immunoreact with the intact protein in its native environment. Second, the natural antibodies of a host to a naturally occurring immunogen, such as a viral protein, rarely immunoreact with a polypeptide that corresponds to a short linear portion of the immunogen's amino acid residue sequence. This latter phenomenon is believed to be the result of short linear polypeptides lacking required secondary and tertiary conformational structures.

Much of the work on the binding of peptide by antibody made to proteins is summarized in a review by Benjamini, E., et al., *Current Topics in Microbiology and Immunology*, 58, 85 (1972). The role of peptide structure in antibody binding has been emphasized by Goodman, J. W., *Immunochem* 6, 139 (1969).

Most of the studies that involve the effects of changes in the sequence of peptides on antibody binding have been interpreted as indicating that the structure of the antibody combining site plays a predominant role. The effect of sequence and structural changes in these studies is intermixed and difficult to segregate. Some of these studies can equally well be explained by structural changes in antigen effecting the binding.

Antibody response at the molecular level involves binding of an antigen of defined sequence (primary structure) and in a defined conformation (secondary and tertiary structure). Immune response to protein antigens has traditionally been interpreted as being directed against primary, secondary or tertiary structue of the protein.

This classification scheme may have some validity for proteins that have a well defined overall structure at physiological temperatures and solutions. However, its validity is in doubt for peptide antigens that have a more dynamic structure.

SUMMARY OF THE INVENTION

The present invention contemplates synthetic polypeptides capable of inducing the production of antibodies that immunoreact with an antigen to a tuberculous mycobacterium. The polypeptides contain about 13 to about 40 amino acid residues and include the amino acid residue sequence, written from left to right and in the direction of amino-terminus to carboxy-terminus, represented by the formula:

AlaLysValAsnIleLysProLeuGluAspLysIle. The polypeptides can include cysteine (Cys) residues at one or both of the amino-terminus and carboxy-terminus.

The polypeptides are capable, when linked to a carrier and introduced in an effective amount into a mammalian host, of inducing production of antibodies that immunoreact with an antigen to a tuberculous mycobacterium. The invention also includes the pharmaceutically acceptable salts and antigenically related variants of the polypeptides.

The polypeptides may also be capable of immunoreacting with human antibodies induced by a natural antigen to a tuberculous mycobacterium.

The present invention also contemplates synthetic multimers containing a plurality of joined synthetic polypeptide repeating units wherein at least one of the repeating units is a polypeptide as described above. The polypeptide repeating units may be joined in a head-to-tail manner by amide bonds. Alternatively, the synthetic polypeptide monomers may be joined by other than amide bonds to form a polymeric multimer such as through the use of intramolecular, interpolypeptide cysteine disulfide bonds.

In another embodiment, an effective amount of a polypeptide of this invention is used in a physiologically tolerable diluent to form an inoculum capable of inducing antibodies that immunoreact with an antigen to a tuberculous mycobacterium. In addition to being used for the production of antibodies, an inoculum of this invention may be used as a vaccine in humans as a means for inducing active immunity to mycobacterial infections.

In still another embodiment, a receptor molecule is contemplated that contains an antibody combining site that is capable of immunoreacting with an antigen to a tuberculous mycobacterium. The receptor is raised to a synthetic immunogen comprising a synthetic polypeptide described above alone or as a conjugate.

Also contemplated is a diagnostic system for assaying for the presence of an antigen to a tuberculous mycobacterium. The system comprises receptor molecules as described above and an indicating means for signaling for the immunoreaction of the combining sites with an antigen to a tuberculous mycobacterium.

Further contemplated is a diagnostic system for assaying for the presence of antibody molecules to an antigen to a tuberculous mycobacterium in a body component. Such a system comprises synthetic polypeptide as described above and an indicating means for signaling the immunoreaction of the polypeptide with the antibody molecules to an antigen to a tuberculous mycobacterium. In a more preferred embodiment, this system also contains a solid support comprised of a solid matrix to which the polypeptide is affixed. A means for identifying the isotype of the immunoreacted antibody molecules may also be included in the system.

In another embodiment, the present invention includes a diagnostic system for determining the presence of cell-mediated immune responsiveness to a tuberculous mycobacterial antigen in a host comprising a synthetic polypeptide as described above that has an amino acid residue sequence that corresponds to the amino acid sequence of a tuberculous mycobacterial antigen. The polypeptide, when administered to a host intradermally in an effective amount and in physiologically tolerable diluent, is capable of inducing the proliferation of thymus-derived cells in the host. The proliferation is indicated by erythema (redness) and intradermal administration.

Methods are also disclosed for inducing the proliferation of thymus-derived cells in a host previously immunized to a tuberculous mycobacterium and for determining the presence of a tuberculous mycobacterial antigen in a host. The methods include the steps of providing a polypeptide as discussed herein and administering intradermally an effective amount of the polypeptide to the host in a physiologically tolerable diluent according to the latter method, the proliferation of thymus-derived cells and the presence of a tuberculous mycobacterial antigen in the host are indicated by erythema and induration at the site of intradermal administration.

The present invention provides several advantages and benefits. One advantage of the present invention is that use of a synthetic polypeptide obviates the need for the presence of its corresponding intact protein. The polypeptide itself may provide a vaccine sufficient to protect the host from disease. Consequently, impurities such as cellular debris and toxins that are associated with the production of usable amounts of viral proteins from bacteria are absent from the product of this invention.

BRIEF DESCRIPTION OF THE DRAWINGS

FIG. 1 illustrates the 20 amino acid residue sequence of the amino-terminal portion of the BCG-a protein of *M. bovis* as determined by Minden et al., *Infect. Immun.*, 46, 516 (1984). Synthetic polypeptides comprising the first 12 amino acid residues of the BCG-a protein are also illustrated. In the first instance, the synthetic polypeptide includes cysteine residue at the carboxy-terminus. In the second instance, the synthetic polypeptide includes cysteine residues at both the amino-terminus and the carboxy-terminus.

DETAILED DESCRIPTION OF THE INVENTION

I. Introduction

Humans infected with tuberculous mycobacteria develop antibodies against antigens associated with the mycobacteria. Traditional clinical techniques used to assay for tuberculous mycobacteria and anti-tuberculous mycobacteria antibodies in humans are cumbersome. In addition, current procedures for the purification of antigens to tuberculous mycobacteria from cell culture are not readily adaptable to mass production.

The present invention contemplates the use of synthetic polypeptide technology to overcome some of the problems of the current methodologies. Relatively short synthetic polypeptides may immunologically mimic antigenic determinants on a natural protein and may therefore be used to raise antibodies of predetermined specificity that recognize the natural protein.

The phrase "immunologically mimics" is used herein to mean that an immunogenic polypeptide of this invention induces production of antibodies that bind to the inducing polypeptide and also to the cognate sequence in the intact protein. This phenomenon may be used both experimentally and clinically.

Experimentally, antibodies to synthetic polypeptides may be used to establish the DNA reading frame, and therefore the amino acid residue sequence of a clinically important protein such as BCG-a protein of *M. bovis*. Clinically, antibodies of predetermined specificity raised to synthetic polypeptides may be used for diagnostic and therapeutic purposes.

Relatively short polypeptides were synthesized whose amino acid residue sequences substantially correspond to that of a tuberculous mycobacterial antigen.

In particular, the invention includes synthetic polypeptides having amino acid residue sequences that substantially correspond to portions of the amino acid residue sequence of the BCG-a protein from *Mycobacterium bovis* strain BCG. This protein was identified by Minden et al., *Infect. Immun.*, 46, 519 (1984), as a protein that is specifically expressed by tuberculous mycobacteria (*M.*

*bovis* and *M. tuberculosis*). As reported in the above publication, Minden et al. determined the sequence of the amino terminal 20 residues of this protein. (See the first amino acid residue sequence of FIG. 1).

According to the present invention, a polypeptide having an amino acid residue sequence that corresponds to residues 1-12 of the BCG-a protein with a cysteine at the carboxy-terminus was synthesized (see the second amino acid residue sequence of FIG. 1) and was shown to elicit a delayed cutaneous hypersensitivity reaction to guinea pigs immunized with a sonic extract of *M. bovis* strain BCG.

In addition, in guinea pigs immunized as described above, a more pronounced delayed cutaneous hypersensitivity reaction was elicited by a polypeptide having an amino acid residue sequence that corresponds to residues 1-12 of the BCG-a protein but includes a cysteine (Cys) residue at both the amino-terminus and the carboxy-terminus. (See the third amino acid residue sequence of FIG. 1).

These results indicate that the polypeptides may be utilized in a skin test to detect with specifity infections of the tuberculous mycobacteria in man. The polypeptides may also be used to circumvent the cross-reactivity problems associated with currently used delayed-type cutaneous hypersensitivity antigens. The present polypeptide may replace tuberculin or PPD as the antigen of choice in DCH tests for the detection of tuberculosis in humans.

A. Synthetic Polypeptides

1. Sequences

The relatively small synthetic polypeptides (13-20 amino acid residues in length) that were used in this study were synthesized using the solid phase method of Merrifield et. al., *J. Am. Chem. Soc.,* 85, 2149 (1963).

The term "synthetic" as used herein means that the polypeptide molecule or polypeptide repeating unit has been built up by chemical means; i.e., chemically synthesized, rather than being prepared by a biological means, as by genetic engineering techniques. Thus, the synthetic polypeptides embodying the present invention are free from naturally occurring proteins and fragments thereof.

The chemically synthesized polypeptides therefore also differ from degradation products of naturally occurring proteins as are prepared by the action of cyanogen bromide on the protein. The well-known solid phase chemical synthesis in which blocked amino acid residues are added in a serial manner to obtain the desired polypeptide is the preferred method of synthesis, and is discussed in greater detail hereinbelow.

All amino acid residues identified herein are in the natural or L-configuration. In keeping with standard polypeptide nomenclature, abbreviations for amino acid residues are as follows:

| SYMBOL | | |
|---|---|---|
| 1-Letter | 3-Letter | AMINO ACID |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |

-continued

| SYMBOL | | |
|---|---|---|
| 1-Letter | 3-Letter | AMINO ACID |
| K | Lys | L-lysine |
| H | His | L-histidine |
| Q | Gln | L-glutamine |
| E | Glu | L-glutamic acid |
| Z | Glx | L-glutamic acid or L-glutamine |
| W | Trp | L-tryptophan |
| R | Arg | L-arginine |
| D | Asp | L-aspartic acid |
| N | Asn | L-asparagine |
| B | Asx | L-aspartic acid or L-asparagine. |
| C | Cys | L-cysteine |

The present invention contemplates a synthetic polypeptide containing about 13 to about 40 amino acid residues and including the sequence defined by the formula written from left to right and in the direction of amino-terminus to carboxy-terminus AlaLysValAsnIleLysProLeuGluAspLysIleCys. The polypeptide is capable, when linked to a carrier and introduced in an effective amount into a mammalian host, of inducing production of antibodies that immunoreact with an antigen to a tuberculous mycobacterium.

The synthetic polypeptides of this invention are often referred to herein simply as "polypeptides" or as "synthetic polypeptides". That usage is for brevity.

The term "antigenically related variants" is used herein to designate polypeptides of differing overall amino acid residue sequence that share at least a portion of one antigenic determinant and are therefore immunologically cross-reactive.

The term "antigenic determinant", as used herein, designates the structural component of a molecule that is responsible for specific interaction with corresponding antibody (immunoglobulin) molecules elicited by the same or related antigen or immunogen.

The term "immunogenic determinant", as used herein, designates the structural component of a molecule that is responsible for the induction in a host of an antibody containing an antibody combining site (idiotype) that binds with the immunogen when used as an antigen.

The term "antigen", as used herein, means an entity that is bound by an antibody.

The term "immunogen", as used herein, describes an entity that induces antibody production in the host animal. In some instances, the antigen and immunogen are the same entity, while in other instances, the two entities are different.

For example, as is described hereinafter, the polypeptide was used to induce production of antibodies in a guinea pig and thus, was used as an immunogen. The antibodies so induced bind to the polypeptide when used as an antigen. The polypeptide was therefore both an immunogen and an antigen. Anti-tuberculous mycobacterium antibodies bind to both the tuberculous mycobacterial antigen as the immunogen and antigen as well as to the polypeptide as antigen.

Preferred embodiments of the present invention are the synthetic polypeptides described herein, the pharmaceutically acceptable salts thereof, and antigenically related variants thereof. Each of those polypeptides is capable of inducing antibodies that bind to antigens to tuberculous mycobacterium, as described above.

It is noted that a dash at the beginning or end of an amino acid residue sequence indicates a bond to a radical such as H and OH, at the amino- and carboxy-termini, respectively, or a further sequence of one or more amino acid residues up to a total of forty amino acid residues in the polypeptide chain.

The phrase "pharmaceutically acceptable salts", as used herein, refers to non-toxic alkali metal, alkaline earth metal and ammonium salts used in the pharmaceutical industry, including the sodium, potassium, lithium, calcium, magnesium and ammonium salts and the like that are prepared by methods well-known in the art. The phrase also includes non-toxic acid addition salts that are generally prepared by reacting the compounds of this invention with a suitable organic or inorganic acid. Representative salts include the hydrochloride, hydrobromide, sulfate, bisulfate, acetate, oxalate, valerate, oleate, laurate, vorate, benzoate, lactate, phosphate, tosylate, citrate, maleate, fumarate, succinate, tartrate, and the like.

B. Multimers

The present invention also contemplates a synthetic multimer containing a plurality of joined synthetic polypeptide repeating units wherein at least one of the repeating units is a polypeptide as described herein.

The multimers of this invention, alone or linked to a carrier, when introduced in an effective amount into a mammalian host, are capable of inducing the production of antibodies that bind to an antigen to a tuberculous mycobacterium. Those multimers that contain the particularly preferred synthetic polypeptide of this invention are also capable of binding human antibodies induced by an antigen to a tuberculous mycobacterium.

Thus, the multimers of this invention, like the polypeptide, are immunogenic, and are antigenic to human anti-tuberculous mycobacterium antibodies. Those multimers may therefore be used to induce the production of anti-tuberculous mycobacterium antibodies that are useful in the diagnostic methods and systems discussed hereinafter, and may also be used as an antigen in appropriate diagnostic methods and systems.

Multimers that contain fewer than about 35 amino acid residues in the total multimer are typically linked to a carrier for use as an immunogen. Those multimers that contain more than a total of about 35 amino acid residues are typically sufficiently immunogenic to be used without a carrier.

Polypeptide multimers may be prepared by bonding together the synthesized polypeptide monomers in a head-to-tail manner using the aforementioned solid phase method; i.e., one complete polypeptide sequence can be synthesized on the resin, followed by one or more of the same or different polypeptide sequences, with the entire multimeric unit thereafter being cleaved from the resin and used as described herein. Such head-to-tail polypeptide multimers preferably contain about 2 to about 4 polypeptide repeating units.

Alternatively, multimers can be prepared as a polymer of synthetic polypeptides used as monomers. As used herein, the term "polymer" in its various grammatical forms is defined as a type of multimer that contains a plurality of synthetic, random copolymer polypeptide repeating units that are joined together by other than peptide bonds.

An exemplary polymer of this invention can be synthesized using a polypeptide of this invention that contains added cysteine residues at both the amino- and carboxy-termini (diCys polypeptide). The diCys polypeptide may be bonded together by intramolecular, interpolypeptide cysteine disulfide bonds utilizing an oxidation procedure to form an immunogenic, antigenic polymer. The polymer so prepared contains a plurality of the synthetic polypeptide of this invention as repeating units. Those repeating units are bonded together by the above-discussed oxidized cysteine (cystine) residues.

The presence of one or two terminal Cys residues in a polypeptide of this invention for the purposes of binding the polypeptide to a carrier or for preparing a polymer is not to be construed as altering the amino acid sequence of polypeptide repeating units of this invention.

C. Inocula

In another embodiment, the polypeptides of this invention are used in a pharmaceutically acceptable diluent to form an inoculum or a vaccine that, when administered in an effective amount, is capable of inducing antibodies that immunoreact with an antigen to a tuberculous mycobacterium.

The word "inoculum" in its various grammatical forms is used herein to describe a composition containing a polypeptide of this invention as an active ingredient used for the preparation of antibodies against tuberculous mycobacteria. When a polypeptide is used to induce antibodies it is to be understood that the polypeptide may be used alone, linked to a carrier or as a multimer, but for ease of expression, these alternatives will not always be expressed hereinafter.

For polypeptides that contain fewer than about 35 amino acid residues, it is preferable to use a carrier for the purpose of inducing the production of antibodies. A polypeptide bound or linked to a carrier will be used illustratively herein where antibodies are being prepared. The inoculum can be used to produce antibodies for use in a diagnostic assays that detect antigens to tuberculous mycobacteria.

The word "vaccine" in its various grammatical forms is used herein to describe a type of inoculum containing a polypeptide of this invention as an active ingredient that is used to induce active immunity in a host mammal. Since active immunity involves the production of antibodies, a vaccine or inoculum may thus contain identical ingredients, but their uses are different. In most cases, the ingredients of a vaccine and of an inoculum are different because many adjuvants useful in animals may not be used in humans.

The present inoculum or vaccine contains an effective amount of a polypeptide of this invention, as a multimer such as a polymer of individual polypeptides linked together through oxidized, polypeptide terminal cysteine residues or as a conjugate linked to a carrier. However, for ease of expression, the various embodiments of the polypeptides of this invention are collectively referred to herein by the term "polypeptide," and its various grammatical forms.

The effective amount of polypeptide per unit dose depends, among other things, on the species of animal inoculated, the body weight of the animal and the chosen inoculation regimen as is well known in the art. Inocula and vaccines typically contain polypeptide concentrations of about 100 micrograms to about 500 milligrams per inoculation (dose). The stated amounts of polypeptide refer to the weight of polypeptide without the weight of a carrier, when a carrier is used. Specific, exemplary inocula are described hereinafter with weight of carrier plus polypeptide (conjugate) being given.

The term "unit dose" refers to physically discrete units suitable as unitary dosages for animals, each unit containing a predetermined quantity of active material calculated to produce the desired therapeutic effect in association with the required diluent; i.e., carrier, or vehicle. The specifications for the novel unit dose of this invention are dictated by and are directly dependent on (a) the unique characteristics of the active material and the particular therapeutic effect to be achieved, and (b) the limitations inherent in the art of compounding such active material for therapeutic use in animals, as disclosed in detail in the specification, these being features of the present invention.

Inocula are typically prepared from the dried solid polypeptide-conjugate or polypeptide polymer by suspending the polypeptide-conjugate or polypeptide polymer in a physiologically tolerable (acceptable) diluent such as water, saline or phosphate-buffered saline.

Inocula may also include an adjuvant. Adjuvants such as complete Freund's adjuvant (CFA), incomplete Freund's adjuvant (IFA) and alum are materials well known in the art, and are available commercially from several sources.

D. Receptors

Antibodies and substantially whole antibodies raised to (induced by) the polypeptides of this invention as well as antibody combining sites prepared from such antibodies constitute still another embodiment of this invention. These molecules are collectively referred to herein as receptors. Receptors are raised in mammalian hosts such as mice, guinea pigs, rabbits, horses and the like by immunization using the inocula described hereinabove.

Suitable monoclonal receptors, typically whole antibodies, may also be prepared using hybridoma technology described by Niman et. al., *Proc. Natl. Acad. Sci. (U.S.A.)*, 80, 4949 (1983), which description is incorporated herein by reference. Briefly, to form the hybridoma from which the monoclonal receptor is produced, a myeloma or other self-perpetuating cell line is fused with lymphocytes obtained from the spleen of a mammal hyperimmunized with a polypeptide of this invention.

It is preferred that the myeloma cell line be from the same species as the lymphocytes. Typically, a mouse of the strain BALB/c is the preferred mammal. Suitable mouse myelomas for use in the present invention include the hypoxanthine-aminopterin-thymidine-sensitive (HAT) cell lines P3X63-Ag8.653 (ATCC CRL 1580), and Sp2/0-Ag14 (ATCC CRL 1581).

Splenocytes are typically fused with myeloma cells using a polyethylene glycol such as PEG 1500 or PEG 6000. Fused hybrids are selected by their sensitivity to HAT. Hybridomas producing the receptor molecules of this invention are identified using the enzyme linked immunosorbent assay (ELISA) described in the Materials and Methods section hereinafter.

Monocloncal receptors need not only be obtained from hybridoma supernatants, but may also be obtained in generally more concentrated form from ascites fluid of mammals into which the desired hybridoma has been introduced. Production of monoclonal antibodies using ascites fluid is well known and will not be dealt with further herein.

A receptor of this invention binds both to the polypeptide to which it was raised and also binds to the corresponding tuberculous mycobacterium antigenic determinant site that the polypeptide of this invention immunologically mimics. Thus, a polypeptide of this invention may be both an immunogen and an antigen.

The receptors of this invention may be described as being oligoclonal as compared to naturally occurring polyclonal antibodies since they are raised to an immunogen having relatively few epitopes as compared to the epitopes of an intact tuberculous mycobacterium antigenic molecule. Consequently, receptors of this invention bind to epitopes of the polypeptide while naturally occurring antibodies raised to antigens of tuberculous mycobacteria bind to epitopes throughout the tuberculous mycobacterium antigenic molecule.

E. Diagnostic Assays Systems and Methods

The polypeptides, antibodies and antibody combining sites (receptors) raised to the before described polypeptides, and methods of the present invention may also be used for diagnostic tests, such as immunoassays. Such diagnostic techniques include, for example, enzyme immune assay, enzyme multipled immunoassay technique (EMIT), enzyme-linked immunosorbent (ELISA), radio-immune assay (RIA), flourescence immune assay, either single or double antibody techniques, and other techniques in which either the receptor or the antigen is labeled with some detectable tag or indicating means. See generally Maggio, *Enzyme Immunoassay*, CRC Press, Cleveland, Ohio (1981); and Goldman, M., *Flourescent Antibody Methods*, Academic Press, New York, N.Y. (1980). Specific examples of such assay methods and systems useful in carrying out those methods are discussed hereinbelow.

1. Assays For Tuberculous Mycobacteria

A method for assaying for the presence of an antigen to tuberculous mycobacteria in a body sample is also contemplated herein. In a general method, a body sample to be assayed is provided, and is admixed with receptor molecules that contain an antibody combining site raised to a synthetic polypeptide of this invention. The admixture is maintained for a predetermined period of time sufficient for the receptor molecules to immunoreact with the antigen to tuberculous mycobacteria present in the body sample. The amount of that immunoreaction is then measured to determine whether the tuberculous mycobacterial antigen was present or absent in the assayed body sample.

An illustrative diagnostic system in kit form embodying one aspect the present invention that is useful for detecting tuberculous mycobacterial antigens present in an aliquot of a body sample contains receptor molecules of this invention such as antibodies, substantially whole antibodies, or antibody combining sites like Fab and F(ab')$_2$ antibody portions raised to a polypeptide of this invention in one package. This system also includes an indicating means for signaling the presence of an immunoreaction between the receptor and the antigen.

Typical indicating means include radioisotopes such as $^{125}$I and $^{131}$I, enzymes such as alkaline phosphatase, horseradish peroxidase, beta-D-galactosidase and glucose oxidase, and fluorochrome dyes such as fluorescein and rhodamine. The indicating means may be linked directly to receptor of this invention. The indicating means may also be linked to a separate molecule such as to a second antibody, to an antibody combining site or to *Staphylococcus aureus* (*S. aureus*) protein A that reacts with (binds to) the receptor of this invention. A specific example of such a separate molecule indicating means is $^{125}$I-labeled *S. aureus* protein A.

The indicating means permits the immunoreaction product to be detected, and is packaged separately from the receptor when not linked directly to a receptor of this invention. When admixed with a body sample such as an acetone-fixed peripheral blood lymphocyte (PBL) smear, the receptor molecule immunoreacts with the tuberculous mycobacterial antigen to form an immunoreactant, and the indicating means present then signals the formation of immunoreaction product.

One embodiment of a diagnostic method for tuberculous mycobacterial antigens is an immunoflourescent assay that includes an amplifying reagent. In such an assay a PBL smear is acetone-fixed to a plain microscope slide. An aliquot of antibodies raised in accordance with this invention, e.g., raised in rabbits or guinea pigs, generally about 100 micrograms to about 500 micrograms, is contacted with the slide using well-known techniques.

After rinsing away any un-immunoreacted antibodies of this invention, any non-specific binding sites on the slide are typically blocked with a protein such as bovine serum albumin (BSA), if desired. A second reagent (amplifying reagent) such as complement, or anti-immunoglobulin antibodies, e.g., guinea pig complement, can then be incubated on the test slide.

After this second incubation, any unreacted of the amplifying reagent is removed as by rinsing leaving only that which is bound to the first-named antibodies on the assay slide. A third reagent (indicating means), e.g., antibody, like goat anti-guinea pig complement, is then incubated on the test slide. The third reagent is labeled by being linked to a flourochrome dye such as fluorescein isothiocyanate (FITC), rhodamine B isothiocyanate (RITC), tetramethylrhodamine isothiocyanate (TRITC), 4, 4'-diisothiocyanostilbene-2,2'-disulfonic acid (DIDS), and the like as are well known in the art.

Any unreacted third reagent is rinsed off after this third incubation, leaving any FITC labeled goat-antiguinea pig complement antibodies that bind to the complement on the test slide. The presence of the FITC labeled third reagent may be detected using flourescence microscopy and thereby signal the presence of mycobacterial infection.

A preferred diagnostic system, preferably in kit form, useful for carrying out the above assay method includes, in separate packages, (a) receptors (antibodies) of this invention that immunoreact with a tuberculous mycobacterial antigen, (b) a second, amplifying reagent such as complement, like guinea pig complement, anti-immunogloulin antibodies or S. aureus protein A that reacts with the receptor, and (c) an indicating means that may be linked directly to the amplifying means or may be a portion of a separate molecule such as an antibody or antibody-portion that reacts with the amplifying reagent. The indicating means indirectly signals the immunoreaction of the receptor molecule and the tuberculous mycobacterial antigen through the mediation of the amplifying reagent.

Receptor molecules and separate indicating means of any diagnostic system described herein, as well as the above-described amplifying reagent, may be provided in solution, as a liquid dispersion or as a substantially dry powder, e.g., in lyophilized form. Where the indicating means is a separate molecule from the amplifying reagent, it is preferred that the indicating means be packaged separately. Where the indicating means is an enzyme, the substrate of the enzyme may also be provided in a separate package of the system. A solid support such as the before-described microscope slide, one or more buffers and acetone may also be included as separately packaged elements in this diagnostic assay system.

The packages discussed herein in relation to diagnostic systems are those customarily utilized in diagnostic systems. Such packages include glass and plastic (e.g., polyethylene, polypropylene and polycarbonate) bottles. vials, plastic and plastic-foil laminated envelopes and the like.

The use of whole, intact, biologically active antibodies is not necessary in many diagnostic systems such as the immunoflourescent assay described above. Rather, only the immunologically active, idiotype-containing, antigen binding and recognition receptor site; i.e., the antibody combining site, of the antibody molecule may be used. Examples of such antibody combining sites are those known in the art as Fab and F(ab')$_2$ antibody portions that are prepared by proteolysis using papain and pepsin, respectively, as is well known in the art.

2. Assays For Anti-Tuberculous Mycobacterial Antibodies

Another diagnostic method of this invention is an ELISA that detecrs anti-tuberculous mycobacterial antibodies (such as anti-BGG-a antibodies) in a body sample. Here, a polypeptide of this invention is used as an antigen, and is preferably bound on (adsorbed to) or otherwise linked to a solid matrix such as the cross-linked dextran available under the trademark SEPHADEX from Pharmacia Fine Chemicals (Piscataway, N.J.), agarose, beads of glass, polyvinyl chloride, polystyrene, cross-linked acrylamide, nitrocellulose or the wells of a microtiter plate to form a solid support.

The polypeptide is admixed with a provided body sample to be assayed. The admixture is maintained for a predetermined time sufficient for anti-tuberculous mycobacterial antibodies present in the body sample to immunoreact with the polypeptide. The presence of that immunoreaction is then determined as with an indicating means to signal the presence of anti-tuberculous mycobacterial antibodies in the assayed body sample.

An exemplary ELISA utilizing the above method uses a solid support comprised of a polypeptide of this invention adsorbed onto a solid matrix comprised of the wells of a twelve or ninety-six well microtiter plate made of polystyrene or polyvinyl chloride. Non-specific binding sites on the microtiter well walls are thereafter typically blocked with a protein such as bovine serum albumin (BSA). Unbound polypeptide and BSA are removed from the microtiter well as by rinsing.

A body sample aliquot such as human serum, blood or plasma is admixed with the above-described polypeptide-bound solid support to form an admixture containing solid and liquid phases. The solid-liquid phase admixture is maintained for a time sufficient for anti-tuberculous mycobacterial antibodies in the body sample to immunoreact with the polypeptide antigen. The solid and liquid phases are thereafter generally separated.

A solution of a second, labeled, indicating means-containing antibody, antibody combining site or S. aureus protein A that reacts with the first-named antibody is then admixed with the solid phase to form another solid-liquid phase admixture. An exemplary second antibody is a peroxidase-labeled goat anti-human Ig antibody where the first-named antibodies are from a human body sample. Additional, useful enzyme labels include alkaline phosphase, beta-D-galactosidase and glucose oxidase. The admixture formed from the solid phase and the second labeled antibody solution is maintained (incubated) for a predetermined time period (e.g., 30 minutes) sufficient to form a reactant between the first-named antibody and the indicating means such as an immunoreaction between the two antibodies. The solid and liquid phases are thereafter separated.

The second antibody described above may also be specific for and immunoreact with only one of the classes of immunoglobulin (e.g., IgG, IgM, IgE, IgA, or IgD). Such antibodies may provide the ability to identify the immunoglobulin class of anti-tuberculous mycobacterial antibody present in the body sample. In addition, the second antibody or antibody combining site may be specific for and immunoreact with only one of the two types of immunoglobulin light chains (e.g., kappa or lambda). These antibodies may provide the ability to identify the isotype of the immunoglobulin molecule present in the body sample.

A solution containing a substrate for the enzyme label such as hydrogen peroxide for peroxidase and a color-forming dye precursor such as o-phenylenediamine, or p-nitrophenyl phosphate for alkaline phosphatase is thereafter admixed with the solid phase. The optical density at a preselected wavelength (e.g., 490 or 405 nanometers, respectively) may then be determined after a predetermined time period has elapsed (e.g., 60 minutes), and compared to the optical density of a control to determine whether anti-tuberculous mycobacterial antibodies were present in the body sample.

Another embodiment of this invention comprises a diagnostic system in kit form that includes a solid support comprised of a solid matrix such as a polystyrene twelve-well microtiter strip, and a polypeptide of this invention, absorbed (bound) or otherwise affixed to the solid matrix to form a solid matrix. This system preferably also includes separately packaged anti-human Ig antibodies having a linked indicating means such as peroxidase-labeled goat anti-human Ig antibodies, and may also include substrate for the linked indicating means such as hydrogen peroxide and a color forming due precursor such as o-phenylenediamine, in further, separate packages. Hydrogen peroxide is typically not included in the kit due to its relative instability, and is typically supplied by the end user. Buffer salts useful in an assay utilizing this system may also be included in one or more separate packages in dry or liquid form. Separate packages containing human anti-tuberculous mycobacterial antibodies and human antibodies free from anti-tuberculous mycobacterial antibodies (normal human antibodies) may also be included as positive and negative controls, respectively. An assay for the presence of anti-tuberculous mycobacterial antibodies in a body sample such as serum may be carried out with this diagnostic system using the above-described method.

II. METHODS AND MATERIALS

A. Synthesis of PolVpeptides

The polypeptides of this invention were chemically synthesized by solid-phase methods as described in Merrifield et. al., *J. Am. Chem. Soc.*, 85, 2149 (1963) and Houghten et. al., *Int. J. Pept. Prot. Res.*, 16, 311 (1980). The solid phase method of polypeptide synthesis was practiced utilizing a Beckman Model 990B Polypeptide Synthesizer, available commercially from Beckman Instrument Co., Berkeley, CA.

For polypeptides having fewer than 35 residues that were used in inocula, a cysteine residue was added to the carboxy-terminus or to both the amino-terminus and the carboxyl-terminus to assist in coupling to a protein carrier as described below. The compositions of all polypeptides were confirmed by amino acid analysis.

In preparing a synthetic polypeptide of this invention by the above solid phase method, the amino acid residues are linked to a resin (solid phase) through an ester linkage from the carboxy-terminal residue. When the polypeptide is to be linked to a carrier via a Cys residue or polymerized via terminal Cys residues, it is convenient to utilize that Cys residue as the carboxy-terminal residue that is ester-bonded to the resin.

The alpha-amino group of each added amino acid is typically protected by a tertiary-butoxycarbonyl (t-BOC) group prior to the amino acid being added into the growing polypeptide chain. The t-BOC group is then removed prior to addition of the next amino acid to the growing polypeptide chain.

Reactive amino acid side chains were also protected during synthesis of the polypeptides. Usual side-chain protecting groups were used for the remaining amino acid residues as follows: O-(p-bromobenzyloxycarbonyl) for tyrosine; O-benzyl for threonine, serine, aspartic acid and glutamic acid; S-methoxybenzyl for cysteine, dinitrophenyl for histidine; 2-chlorobenzoxycarbonyl for lysine and tosyl for arginine.

Protected amino acids were recrystallized from appropriate solvents to give single spots by thin layer chromatography. Couplings were typically carried out using a ten-fold molar excess of both protected amino acid and dicyclohexyl carbodiimide over the number of milliequivalents of initial N-terminal amino acid. A two molar excess of both reagents may also be used. For asparagine, an equal molar amount of N-hydroxy-benzotriazole was added to the protected amino acid and dimethyl formamide was used as the solvent. All coupling reactions were more than 99% complete by the picric acid test of Gisin, *Anal. Chem. Acta.*, 58, 248 (1972).

After preparation of a desired polypeptide, a portion of the resulting, protected polypeptide (about 1 gram) was treated with two milliliters of anisole, and anhydrous hydrogen flouride, about 20 milliliters, was condensed into the reaction vessel at dry ice temperature. The resulting mixture was stirred at about 4 degrees C. for about one hour to cleave the protecting groups and to remove the polypeptide from the resin. After evaporating the hydrogen flouride at a temperature of 4 degrees C. with a stream of $N_2$, the residue was extracted with anhydrous diethyl ether three times to remove the anisole, and the residue was dried in vacuo.

The vacuum dried material was extracted with 5 percent aqueous acetic acid (3 times with 50 milliliters) to separate the free polypeptide from the resin. The extract-containing solution was lyophilized to provide a monomeric unoxidized polypeptide.

The produced synthetic polypeptide may be used as a reagent in an enzyme-linked immunosorbent assay (ELISA) to detect anti-tuberculous mycobacterial antibodies. The synthetic polypeptide may also be used to produce an inoculum, usually by linking it to a carrier to form conjugate and then dispersing an effective amount of the conjugate in a physiologically tolerable diluent, as is discussed hereinafter.

It is also to be noted that a synthetic multimer of this invention can be prepared by the solid phase synthesis of a plurality of the polypeptides of this invention linked together end-to-end (head-to-tail) by an amide bond between the carboxyl-terminal residue of one polypeptide and the amino-terminal residue of a second polypeptide. Such synthetic multimers are preferably synthesized as a single long polypeptide multimer, but can also be prepared as individual polypeptides that are linked together subsequent to their individual syntheses, using a carbodiimide reagent such as 1-(3-dimethylaminopropyl)-3-ethyl-carbodiimide hydrochloride in water. The total number of amino acid residues contained in a multimer prepared as a single polypeptide chain is preferably less than about 50, so that up to about eight polypeptides of this invention can be incorporated into a single head-to-tail multimer chain that is synthesized as a single polypeptide. A synthetic head-to-tail multimer more preferably contains two to about four blocks of linked, synthetic, random copolymer polypeptides of this invention, and a total of less than about 40 amino acid residues.

B. Preparation of Polymers

The polypeptides of the present invention may be connected together to form an antigenic and/or immunogenic polymer (synthetic multimer) comprising a plurality of the polypeptide repeating units. Such a polymer typically has the advantage of increased immunogenicity and antigenicity. In addition, a carrier is typically not needed when a polymeric immunogen is utilized. Where different polypeptide monomers are used to make up the polymer, the ability to immunoreact with antibodies to several tuberculous mycobacterial antigenic determinants is obtained. A still further advantage is the ability of such a polymer when used in an inoculum to induce antibodies that immunoreact with several antigenic determinants of a tuberculous mycobacterial antigen.

A polymer of this invention may be prepared by synthesizing the polypeptides as discussed above and including cysteine residues at both the amino- and carboxy-termini to form a "diCys-terminated" polypeptide. After synthesis, in a typical laboratory preparation, 10 milligrams of the diCys polypeptide (containing cysteine residues in un-oxidized form) are dissolved in 250 milliliters (ml) of 0.1 molar (M) ammonium bicarbonate buffer. The dissolved diCys-terminated polypeptide is then air oxidized by stirring the resulting solution gently for a period of about 18 hours in the air, or until there is no detectable free mercaptan by the Ellman test. [See Ellman, *Arch. Biochem. Biophys.*, 82, 70 (1959).]

The polymer (synthetic multimer) so prepared contains a plurality of the synthetic, random copolymer polypeptide repeating units that are bonded together by oxidizing cysteine (cystine) residues. Such polymers typically contain their polypeptide repeating units bonded together in a head-to-tail manner as well as in head-to-head and tail-to-tail manners; i.e., the amino-termini of two polypeptide repeating units may be bonded together through a single cystine residue as may two carboxyl-termini since the linking groups at both polypeptide termini are identical.

C. Coupling To Carriers

The synthetic polypeptides were coupled to keyhole limpet hemocyanin (KLH) as carrier by the method described in Liu et al., *Biochem.*, 80, 690 (1979). Briefly, 4 milligrams (mg) of the carrier were activated with 0 51 mg of m-maleimidobenzoyl-N-hydroxysuccinimide ester, and were subsequently reacted with 5 mg of the polypeptide through an amino- or carboxy-terminal cysteine to provide a conjugate containing about 10 to about 35 percent by weight polypeptide.

One or more additional amino acid residues may be added to the amino- or carboxy- termini of the synthetic polypeptide to assist in binding the polypeptide to a carrier. As discussed before, cysteine residues added at the amino- or carboxy-termini of the synthetic polypeptide have been found to be particularly useful for forming polymers via disulfide bonds. However, other methods well known in the art for preparing conjugates can also be used. Exemplary additional linking procedures include the use of Michael addition reaction products, dialdehydes such as glutaraldehyde, Klipstein et al., *J.Infect. Dis*, 147, 318 (1983) and the like, or the use of carbodiimide technology as in the use of a water-soluble carbodiimide to form amide links to the carrier, as discussed before for linking a plurality of polypeptides together to form a synthetic multimer.

Useful carriers are well known in the art, and are generally proteins themselves. Exemplary of such carriers are keyhole hemocyanin (KLH), edestin, thyroglobulin, albumins such as bovine serum albumin (BSA) or human serum albumin (HSA), red blood cells such as sheep erthrocytes (SRBC), tetanus toxoid, cholera toxoid as well as polyamino acids such as poly (D-lysine:D-glutamic acid), and the like.

As is also well known in the art, it is often benefical to bind a synthetic polypeptide to its carrier by means of an intermediate, linking group. As noted above, glutaraldehyde is one such linking group. However, when cysteine is used, the intermediate linking group is preferably an m-maleimidobenxoyl N-hydroxy succinimide (MBS), as was used herein.

Additionally, MBS may be first added to the carrier by an ester-amide interchange reaction as disclosed by Liu et al., supra. Thereafter, the addition can be followed by addition of a blocked mercapto group such as thiolacetic acid ($CH_3COSH$) across the maleimido-double bond. After cleavage of the acyl blocking group, a disulfide bond is formed between the deblocked linking group mercaptan and the mercaptan of the added cysteine residue of the synthetic polypeptide.

The choice of carrier is more dependent upon the ultimate use of the immunogen than upon the determinant portion of the immunogen, and is based upon criteria not particularly involved in the present invention. For example, if a inoculum is to be used in animals, a carrier that does not generate an untoward reaction in the particular animal should be selected.

D. ELISA

Anti-polypeptide antibody binding and inhibition studies may be prepared by an enzyme-linked immunosorbent assay (ELISA) as described below.

Briefly, microtiter wells (Costar, #3590, Cambridge, MA) are coated with individual polypeptides as antigens by adding 100 microliters (ul) of BBS [10 millimoler (mM) sodium borate (pH 8.3), 150 mM NaCl] containing polypeptide at a concentration of 10 micrograms per milliliter (ug/ml). Contact between the wells and antigen-containing solution is maintained for a predetermined time, typically 15 minutes, and at 20 degrees C., to form an antigen-coated solid phase. The solid and liquid phases are separated and the wells are washed three times with BBS.

Non-specific binding sites are blocked by admixing 200 microliters of 1 percent bovine serum albumin (BSA) in each well to form another solid-liquid phase admixture, and maintaining that solid-liquid phase admixture for 30 minutes, at 20 degrees C. The phases are separated and excess, unbound BSA is removed by washing three times with BBS.

Rabbit (or guinea pig) and human sera (body sample aliquots) are assayed for anti-polypeptide activity by adding 100 microliters of a serum diluted 1:20 in BBS per well to form a solid/liquid phase composition. Contact between the diluted sera and the antigen-coated solid phase is maintained for a predetermined time such as 1 hour, and at 20 degrees C., for an immunoreactant to form. The solid and liquid phases are separated, and the solid phase; i.e., antigen-coated, immunoreactant containing wells, is then washed three times with BBS.

The antibodies in human sera that immunoreact with an adsorbed polypeptide may be detected using an indicating means comprising alkaline phosphatase-conjugated goat anti-human Ig antibody (Tago, Burlington, CA). The antibodies in rabbit sera that immunoreact with an adsorbed polypeptide may be detected using an indicating means comprising alkaline phosphatase-conjugated goat anti-rabbit Ig antibody (Kirkegard & Perry Laboratories, Inc., Gaithersburg, MD). In either instance, 100 microliters of the indicating antibody diluted 1:300 in BBS are added per well to form a further solid-liquid phase composition. This solid-liquid phase composition is maintained for a predetermined time, one hour, for the formation of a reaction product between the human antibodies bound to the solid phase and the indicating means, and at 20 degrees C. The phases are separated, and the solid phase is washed 3 times with BBS.

Alkaline phosphatase-conjugated antibody bound to polypeptide specific antibody may be detected by spectrophotometrically measuring the enzymatic hydrolysis of p-nitrophenyl phosphate to p-nitrophenol. Briefly, 100 microliters of p-nitrophenyl phosphate [1 milligram per milliliter in 2 mM magnesium chloride (pH 9.8), 50 mM sodium carbonate]are added to each well. The enzymatic reaction is allowed to proceed 1 hour and then the optical density at 405 nm is determined in a TITERTEK spectrophotometer available from Flow Laboratories, Inglewood, CA.

E. Immunizations

The receptor molecules of this invention include whole antibodies raised in mammals by immunizing them with inocula including a polypeptide and/or multimer as described hereinabove. Both polypeptides and multimers may be used included in inocula alone or conjugated to a carrier protein such as keyhole limpet hemocyamin (KLH). However, polypeptides are preferably used as a conjugate and multimers are preferably used alone.

Rabbits may be immunized with inocula containing 1.0 mg of conjugate in complete Freund's adjuvant (CFA), and boosted one month later with 1.0 mg of conjugate in incomplete Freund's adjuvant (IFA). Each immunization consisted of one subcutaneous injection, on the back hip. Rabbits were bled 1 and 2 months subsequent to the boost.

Sera containing immunologically active antibodies were then produced from the bleeds by methods well known in the art. These antibodies immunoreacted with one or more of the polypeptides of this invention, and a tuberculous mycobacterial antigenic determinant. They may thus be used in a system to determining the presence of mycobacterial infections.

Individual inocula are prepared with CFA or IFA as follows: An amount of conjugate sufficient to provide the desired amount of polypeptide per inoculation (e.g., 1 mg) is dissolved in PBS (at about 0.5 ml) at pH 7.2. Equal volumes of CFA or IFA are then mixed with the conjugate solutions to provide an inoculum containing conjugate, water and adjuvant in which the water to oil ratio was 1:1. The mixture is thereafter homogenized to provide the inocula. The volume of an inoculum so prepared is typically greater than 1 ml, and some of the conjugate, PBS and adjuvant may be lost during the emulsification. Substantially all of the emulsion that can be recovered is placed into a syringe, and then is introduced into the rabbits as discussed before. The amount of inoculum introduced into the rabbits should be at least about 90 percent of that present prior to the emulsification step.

The above inocula stock solutions are illustrative of the inocula of this invention. As demonstrated herein, they may be used to produce receptor molecules that immunoreact with tuberculous mycobacterial antigens.

F. Delayed-Type Hypersensitivity Reaction (Skin Reaction Test)

The previously described diagnostic systems and assays are based on in vitro assays. Although particular steps of the assays can be carried out in vivo, the actual immune response is measured in tissue culture. The present invention, however, can also be applied to diagnostic systems involving the in vivo measurement of T cell responses. One example of such a system is a delayed-type cutaneous hypersensitivity (DCH) reaction or what is more commonly known as a skin reaction test.

A DCH reaction can only occur in an individual previously exposed (sensitized) to a given antigen. The first exposure of an individual to the antigen produces no visible change, but the immune status of the individual is altered in that hypersensitivity to renewed exposure to that antigen results. Thus, upon intradermal or subcutaneous injection of the antigen (preferably in a buffered saline solution) a characteristic skin lesion develops at the injection site—a lesion that would not develop after a first antigen exposure. Because the response to the second (or challenge) antigen inoculum is typically delayed by 24 to 48 hours, the reaction is referred to as delayed-type hypersensitivity.

In humans, exposure to a sensitizing antigens takes place upon contact with the microorganism responsible for the disease (e.g , tuberculin from *Mycobacterium tuberculosis*, typhoidin from *Salmonella typhi* and abortin from *Brucella abortus*), and sensitization occurs as a result of a chronic infection. In animals, sensitization can be achieved by inoculation of an antigen emulsified in water, saline or an adjuvant.

In both humans and animals, hypersensitivity is tested in vivo by the injection of the antigen dissolved in a physiologically tolerable diluent such as saline solution into the skin (either intradermally or subcutaneously). DCH is usually a more sensitive diagnostic assay than the determination or measurement of the amount of antibody produced to an antigen. For example, only minute amounts of protein (a few hundred micrograms) are necessary for DCH sensitization of a mouse, while a much larger dose is needed to induce antibody production.

Since the polypeptides of the present invention stimulate the proliferation of guinea pig T cells following immunization (sensitization) with a polypeptide of the invention, a skin reaction test was developed using one or more of the present synthetic polypeptides as a challenge antigen.

In particular, a delayed-type cutaneous hypersensitivity reaction was observed when a synthetic polypeptide of this invention was administered intradermally to Mycobacterium bovis BCG-sensitized and Mycobacterium tuberculosis strain H37Rv-sensitized guinea pigs.

The bacteria described herein were obtained from the culture collection of the Scripps Clinic and Research Foundation and were grown as described in Minden et al., Science, 176, 57 (1972) and Minden et al., *Infect. Immun.,* 6, 574 (1972), which publications are incorporated herein by reference.

In particular, guinea pigs that were immunized about six weeks earlier with heat-killed BCG-containing or H37Rv-containing cell sonicates demonstrated a delayed cutaneous hypersensitivity (DCH) reaction upon intradermal infection of about 250 micrograms of a synthetic polypeptide. The polypeptide was typically administered in about 100 microliters of phosphate-buffered saline (pH 7.0) containing 0.005 percent TWEEN 20.

In conventional practice, a DCH reaction is sought at 24 and 48 hours after injection of an antigen. The inflammatory infiltrate (consisting primarily of mononuclear cells), which occurs 24–48 hours following intradermal injection of the antigen, and the accompanying edema produce induration of the skin. A coexistent area of erythema may also develop. The diameter of this induration is an index of cutaneous hypersensitivity, and an induration of about 5 millimeters or more in diameter is the generally accepted criterion of a positive DCH reaction.

Polypeptides of the invention elicited an erythematous area and an induration of at least about 10 millimeters in diameter about the injection site. Unimmunized animals demonstrated no DCH reaction upon intradermal injection of a polypeptide. Animals immunized with cell extracts of nontuberculous mycobacteria demonstrated marginal DCH reactions (erythemas and indurations of less than about 5 millimeters) to a polypeptide.

The polypeptide that elicited the most pronounced DCH reactions was polymerized through cysteine residues at both its amino-terminus and carboxy-terminus. See the diCys polypeptide shown at line 3 of FIG. 1. The results of DCH tests using that polypeptide are shown in Table 1.

TABLE I

| Animals Immunized With Sonicates[1] Of The Following | DCH[2] Reaction To 250 Micrograms Of Polypeptide[3] | DCH Reaction To PPD[5] |
|---|---|---|
| *M. Bovis* strain BCG | 7/7[4] | 7/7 |
| *M. tuberculosis* strain H37Rv | 4/4 | 4/4 |
| *M. fortuitum* | 0/4 | 4/4 |
| *M. kansasii* | 0/3 | 3/3 |
| *M. intracellulare* | 2/4 | 4/4 |
| Polypeptide (diCys Terminated) (see Note 3) | 5/5 | 0/5 |

TABLE I-continued

| Animals Immunized With Sonicates[1] Of The Following | DCH[2] Reaction To 250 Micrograms Of Polypeptide[3] | DCH Reaction To PPD[5] |
|---|---|---|
| Unimmunized Animals | 0/5 | 0/5 |

[1]Prepared and immunized as described in Minden et al., Infect. Immun., 46, 519 (1984), which is incorporated herein by reference.
[2]Delayed-type cutaneous hypersensitivity.
[3]250 micrograms of a polypeptide having the amino acid residue sequence -CysAlaLysValAsnIleLysProLeuGlnAsp-LysIleCys (The polypeptide shown at line 3 of FIG. 1) were dissolved in about 100 microliters of phosphate-buffered saline (pH 7.0) containing about 0.005 percent TWEEN 20 (ICI Americas, Inc., Wilmington, D).
[4]The first numeral in each series represents the number of positive DCH reactions and the second numeral represents the total number of trials.
[5]PPD (Purified Protein Derivative) from Connaught Laboratories LTD., Willowdale, Canada was administered in 100 microliter quantities which is equivalent to about 250 tuberculin units.

Referring to Table I, guinea pigs immunized with cell sonicates of *M. bovis* strained BCG or *M. tuberculosis* H37Rv strain developed a strong DCH reaction to the polypeptides and to PPD (purified protein derivative).

Animals immunized with nontuberculous mycobacteria (*M. fortuitum, M. kansasii* and *M. intracellulare*) developed a weak reaction or did not react (See Table I for particulars) to the polypeptides, but developed a strong DCH reaction to PPD.

Animals immunized with the diCys-terminated polypeptide developed a DCH reaction to the polypeptide, but not to PPD.

Unimmunized normal animals developed no DCH reaction to the polypeptides or to PPD.

The immunogenicity of the present polypeptides was also investigated using the polypeptides to elicit antibodies. The specificities and binding characteristics were determined of the resulting antibodies in an enzyme-linked immunosorbent assay (ELISA) as described herein.

A strong anti-polypeptide response was elicited when the polypeptide (shown at line 2 of FIG. 1) was coupled to a protein carrier (keyhole limpet hemocyanin) and injected into rabbits along with incomplete Freund's adjuvant. The titer of the resulting antisera against the polypeptide was measured by immobilizing 1 microgram of the polypeptide in each well of a polystyrene microtiter plate and then reacting the bound polypeptide with serial dilutions of the antisera. Antibody titer is expressed as the reciprocal of the dilution of antibody that produces 50 percent maximal binding in the ELISA. The antisera had anti-polypeptide titers of 1250–2500.

The reactivity of the polypeptide-elicited antibodies with extracts of various mycobacterial species was measured in an ELISA in which "S antigen" preparations were immobilized in the wells of the polystyrene microtiter plates. ["S antigens" are the antigens present in the supernatant fractions following centrifugation at 100,000xg of bacterial suspensions that had been disrupted by sonication. As described by Minden et al., *Infect. Immun.,* 46, 519([1984), which is incorporated herein by reference].

In the case of the polypeptide having an amino acid residue sequence that corresponds to residues 1–12 of the BCG-a protein with a cysteine at the carboxy-terminus, the anti-polypeptide antibodies reacted strongly with the polypeptide (titer=1250), purified BCG-a protein (1250), and soluble sonicated extracts of *Mycobacterium bovis* strain BCG (675) and *Mycobacterium tuberculosis* strain H37Rv (675). Only marginal binding to the sonicated extracts of *Mycobacterium fortuitum*

(50), *Mycobacterium kansasii* (25), and *Mycobacterium intracellulare* (25) was observed. This sort of marginal binding was also seen with the pre-immune rabbit serum, suggesting that the rabbit antibodies might be non-specifically sticking to these mycobacterial extracts. There was no binding (titer less than 10) to the "S antigens" of *E. coli, Listeria monocytogenes, Salmonella epidermis, Salmonella typhimurium,* or *Pseudamonas sp.* These data indicate that the polypeptide contains an immunogenic epitope that is expressed predominantly in the tuberculous mycobacterial species.

The antigenicity of the polypeptides was determined in two ways. First, to measure the reactivity with humoral antibodies, the polypeptides were immobilized onto wells of a microtiter plate and reacted with various antibody preparations. In the case of the polypeptide having an amino acid residue sequence that corresponds to residues 1–12 of the BCG-a protein with a cysteine at the carboxy-terminus, there was significant binding to the polypeptide by antibodies directed against the polypeptide (titer=1250), BCG-a protein (625), and a whole sonicate extract of *M. bovis* BCG (625). There was only marginal binding by the antibodies elicited by extracts of *M. kansaii* (25) and *M. fortuitum* (5). There was no detectable binding to antisera elicited by extracts of *E. coli, L. monocytogenes, S. epidermis, S. typhimurium,* or *Pseudamonas sp.* Once again, the data suggest that this epitope is expressed mainly by the tuberculous species and poorly if at all by the two atypical strains tested. (*M. kansaii* and *M. fortuitum*).

The results of the DCH reactions demonstrate that the synthetic polypeptides of the present invention may be useful in an in vivo diagnostic system for the presence of a cell mediated immune response to tuberculous mycobacterial antigens.

After the safety and effectiveness of the above polypeptides are shown in animal studies, the polypeptides can be used as challenge antigens in human skin reaction tests for recipients of tuberculous mycobacterial vaccines. The polypeptides are synthesized as previously described, purified by high pressure liquid chromatography (HPLC) techniques, sterilized and pyrogen-tested.

Since the T cell proliferative responses of human tuberculous mycobacterial vaccine recipients can be quite variable relative to polypeptide specificity, vaccine recipients and individuals serving as unvaccinated controls are challenged with a series of polypeptides. The kinetics and optimal antigen dose can be determined in the vaccine recipient group using the results from the animal studies as a guideline.

Chronically infected individuals can also be studied for tuberculous mycobacterial-specific T cell sensitization using synthetic polypeptides as antigens for a skin reaction test.

In each instance, the challenge antigen is administered by intradermal injection of the particular polypeptide in a physiologically acceptable solution (about 1 milliliter) into the volar surface of the forearm. Use of a 25- or 27-gauge needle usually assures intradermal rather than subcutaneous administration of the antigen. Subcutaneous injection can lead to dilution of the antigen in tissues and can produce a false-negative test. The injection sites are then observed for erythema (skin reddening) and induration (swelling) at 4, 24 and 48 hours post-challenge.

The foregoing is intended as illustrative of the present invention but not limiting. Numerous variations and modifications may be effected without departing from the true spirit and scope of the novel concepts of the invention. It is to be understood that no limitation with respect to the specific polypeptides, antibodies, their compositions and uses illustrated herein is intended or should be inferred.

What is claimed is:

1. A synthetic polypeptide containing about 13 to about 40 amino acid residues and including the thirteen amino acid residue sequence, written from left to right and in the direction from amino-terminus to carboxy-terminus, represented by the formula:

AlaLysValAsnIleLysProLeuGluAspLysIleCys;

said polypeptide being capable of inducing the production of antibodies that immunoreact with an antigen to a tuberculous mycobacterium when linked to a carrier and introduced in an effective amount into a mammalian host.

2. A synthetic polypeptide inoculum suitable for inducing antibodies that immunoreact with an antigen to a tuberculous mycobacterium that comprises a synthetic polypeptide containing about 13 to about 40 amino acid residues dissolved or dispersed in an effective amount in a pharmaceutically acceptable diluent, said polypeptide including the thirteen amino acid residue sequence, written from left to right in the direction of the amino-terminus to carboxy-terminus, represented by the formula:

AlaLysValAsnIleLysProLeuGluAspLysIleCys;

said inoculum when introduced in an effective amount into a mammalian host being capable of inducing the production of antibodies that immunoreact with an antigen to a tuberculous mycobacterium.

3. The synthetic polypeptide inoculum of claim 2 wherein said polypeptide is bound to a carrier.

4. A synthetic polypeptide inoculum according to claim 2 in unit dosage form wherein the polypeptide is present in an amount of about 100 micrograms to about 500 milligrams per dose.

5. A synthethic polypeptide having the amino acid residue sequence, written from left to right and in the direction from amino-terminus to carboxy-terminus, represented by the formula:

CysAlalysValAsnIleLysProLeuGluAspLysIleCys;

said polypeptide being capable of inducing the production of antibodies that immunoreact with an antigen to a tuberculosis mycobacterium when linked to a carrier and introduced in an effective amount into a mammalian host.

6. A synthetic multimer containing a plurality of joined synthetic polypeptide repeating units, said repeating units comprising at least one synthetic polypeptide containing about 14 to about 40 amino acid residues and including an amino acid residue sequence, written from left to right and in the direction from amino-terminus to carboxy-terminus, represented by the formula:

AlaLysValAsnIleLysProLeuGluAspLysIleCys; and

CysAlaLysValAsnIleLysProLeuGluAspLysIleCys;

said polypeptide repeating units being capable of inducing the production of antibodies that immunoreact with an antigen to a tuberculous mycobacterium when linked to a carrier and introduced in an effective amount into a mammalian host.

7. The multimer according to claim 6 wherein said polypeptide repeating units are joined together by an amide or disulfide bond.

8. A synthetic inoculum suitable for inducing antibodies that immunoreact with an antigen to a tuberculous mycobacterium that comprises a synthetic multimer containing a plurality of joined synthetic polypeptide repeating units, said repeating units comprising at least one synthetic polypeptide containing about 14 to about 40 amino acid residues dissolved or dispersed in an effective amount in a pharmaceutically acceptable diluent, said polypeptide including the amino acid residue sequence, written from left to right in the direction of the amino-terminus to carboxy-terminus, represented by the formula:

CysAlaLysValAsnIleLysProLeuGluAspLysIleCys;

said inoculum when introduced in an effective amount into a mammalian host being capable of inducing the production of antibodies that immunoreact with an antigen to a tuberculous mycobacterium.

9. The synthetic inoculum of claim 8 wherein said multimer is bound to a carrier.

10. A synthetic inoculum according to claim 8 in unit dosage form wherein the multimer is present in an amount of about 10 micrograms to about 500 milligrams per dose.

* * * * *

UNITED STATES PATENT AND TRADEMARK OFFICE
CERTIFICATE OF CORRECTION

PATENT NO. : 4,689,397
DATED : August 25, 1987
INVENTOR(S) : Thomas M. Shinnick, Percy Minden and Richard S. Houghten It is certified that error appears in the above-identified patent and that said Letters Patent is hereby corrected as shown below:

Column 1,
Line 5, insert:
-- This invention was made with government support under Grant No. AI 22217 from the National Institutes of Health. The U.S. government may have certain rights in the invention. --

Signed and Sealed this

Twenty-first Day of May, 2002

*Attest:*

JAMES E. ROGAN
*Attesting Officer*    Director of the United States Patent and Trademark Office